United States Patent [19]

Isley et al.

[11] 4,263,805
[45] Apr. 28, 1981

[54] SOLID IMPURITY DETECTOR

[75] Inventors: Walter F. Isley; Joseph L. Dodd, both of Muskegon, Mich.

[73] Assignee: Teledyne Industries, Inc., Los Angeles, Calif.

[21] Appl. No.: 83,287

[22] Filed: Oct. 10, 1979

[51] Int. Cl.³ ............................................. G01N 15/00
[52] U.S. Cl. ...................................... 73/38; 73/61 R; 210/387
[58] Field of Search .................... 73/38, 61 R, 61.1 R; 116/268, DIG. 25; 210/387

[56] References Cited

U.S. PATENT DOCUMENTS

| 1,844,611 | 2/1932 | Spackman | 210/387 X |
| 2,675,697 | 4/1954 | Quynn et al. | 73/61 R X |
| 3,167,949 | 2/1965 | Stenzel et al. | 73/61 R X |
| 3,672,507 | 6/1972 | Paull, Jr. | 210/387 X |
| 3,912,632 | 10/1975 | Winzen | 210/387 X |
| 4,117,717 | 10/1978 | Isley | 73/38 |

Primary Examiner—Gerald Goldberg
Assistant Examiner—Joseph W. Roskos
Attorney, Agent, or Firm—Gifford, Vanophem, Sheridan & Sprinkle

[57] ABSTRACT

A device is provided for detecting the presence of solid impurities within a pressurized fluid. The device comprises a housing having a fluid passageway formed therein. One end of the fluid passageway is open to the pressurized fluid while the other end of the fluid passageway is open to a low pressure fluid region via a restricted port. A filter strip dispensed from a filter strip magazine is disposed across and obstructs the fluid flow through the passageway at a point intermediate its ends so that the filter strip removes solid or liquid particles from fluid flowing through the passageway. A differential pressure sensing means, such as a differential pressure transducer, communicates with the fluid passageway and detects the differential pressure across the filter strip. An increase of fluid pressure sensed by the differential pressure sensing means is indicative of a clogged filter strip which, in turn, indicates the presence of solid impurities within the pressurized fluid. Appropriate indicating means are coupled to the differential pressure sensing means to provide a signal upon the occurrence of a clogged condition of the filter strip.

9 Claims, 2 Drawing Figures

SOLID IMPURITY DETECTOR

BACKGROUND OF THE INVENTION

I. Field of the Invention

The present invention relates to a device for detecting solid or liquid impurities within a pressurized fluid and, more particularly, to such a device which utilizes a filter strip area to trap said impurities and means for measuring an increase in the differential pressure across the filter strip area as it becomes clogged.

II. Description of the Prior Art

In internal combustion engines, and particularly turbocharged diesel engines, dust ingestion by the engine has proven to be a very acute problem. Dust ingestion by the engine not only adversely affects the performance of the engine, but also abrades and damages the engine components, most notably the engine pistons, valves, piston rings and cylinders. Engine damage resulting from dust ingestion, of course, is not only expensive to repair and results in downtime for the engine, but also in the case of military vehicles, an inoperable engine caused by dust ingestion may result in capture of the military vehicle.

In order to prevent, or at least minimize, dust ingestion by the engine, a number of previously known means have been devised to separate dust and other solid particles from the airflow inducted into the engine. For example, filtering systems utilizing filter media are conventionally disposed at the air intake for the engine to separate dust particles from the inducted engine air. A still further type of filtering system for removing dust particles from the induced air is described in U.S. Pat. No. 4,177,717, and which is commonly owned with the instant application. In any event, all of these previously known systems in one fashion or another remove or separate the dust particles from the air inducted into the engine.

These previously known air filtering systems, however, can fail which results in the induction of dust particles into the internal combustion engine. For example, filter media often becomes clogged with dust which decreases the efficiency of the filter media and which permits dust particles to pass therethrough. At other times the filter media becomes torn or damaged which, likewise, results in dust ingestion by the engine. In either event, the filter media must, at the very least, be cleaned and/or replaced.

The previously known internal combustion engines, however, have usually not included means for detecting the failure of the engine filtering system, but rather have relied upon periodic maintenance to inspect the filters. Such periodic maintenance checks, however, often are performed subsequent to the failure of the engine filtering system. Consequently, the engine ingests dust between the time of the air cleaner failure and the time of the maintenance check. Such dust ingestion, of course, damages the engine in the previously described fashion.

One previously known solid impurity detector is disclosed in U.S. Pat. No. 4,117,717, issued on Oct. 3, 1978, and which is commonly owned with the instant application. In this prior device, however substantial disassembly of the engine housing is required to replace its individual filter element, when clogged. Thus, a store of clean individual elements was required. Moreover, this prior device only sensed absolute pressure on one side of the filter element rather than the differential pressure across the filter element which can result in false readings due to engine pressure variations.

SUMMARY OF THE PRESENT INVENTION

The present invention overcomes the above-mentioned disadvantages by providing a device for detecting solid or liquid impurities within a pressurized fluid and which is particularly adapted for use at the air intake of an internal combustion engine.

In brief, the device of the present invention comprises a housing having a fluid passageway formed therethrough. One end of the fluid passageway is open to a relatively high pressure fliud region while the other end of the passageway is opened to a relatively low pressure region so that fluid flows through the passageway from the high to the lower pressure region. The end connected to the low pressure region is provided with a suitable restriction to limit the fluid flow through the passageway. In the preferred form of the invention, one end of the fluid passageway is open to the outlet of an engine turbocharger while the other end of the passageway is open to the turbocharger inlet.

A coiled filter strip dispensed with or without a filter strip magazine is disposed across the passageway at a point intermediate the ends of the passageway so that the entire fluid flow through the passageway passes through the exposed area of the filter strip. The filter strip area, thus, filters and retains any dust particles or other solid or liquid impurities present in the fluid flow.

A differential pressure sensing means, such as a differential pressure transducer, senses the pressure on both sides of the filter strip exposed area and thus senses the pressure drop across the filter strip area. The output of the differential pressure sensing means is coupled to any appropriate means for indicating the magnitude of the differential pressure across the filter strip area.

In operation and assuming a relatively clean filter strip area within the fluid passageway, the differential pressure sensed by the differential pressure sensing means remains relatively constant and at a predetermined low magnitude. However, in the event that dust particles or solid or liquid impurities are present within the pressurized fluid, these impurities are removed by the exposed filter strip area from the fluid flow through the passageway. The filter strip area becomes increasingly clogged with impurities and this increases the pressure drop across the filter strip which is sensed by the differential pressure sensing means. The differential pressure sensing means, in turn, activates the indicating means which warns the operator that a failure of the engine air filtering system has occurred. The operator can then immediately take appropriate action to either clean, repair, or replace the engine filtering system in order to prevent damage to the internal combustion engine.

Following repair or cleaning of the engine filtering system, a clean filter area is positioned across the fluid passageway by simply loosening the engine housing part containing the coiled filter strip, pulling the filter strip outwardly from the housing part so that a clean filter strip area from the magazine is positioned across the fluid passageway, and then retightening the housing part. The coiled filter strip presents a multitude of filter areas stored in a replaceable magazine.

Thus, unlike the previously known internal combustion engines, the device of the present invention provides a means for immediately indicating the failure of the engine air filtering system thereby effectively preventing engine damage caused by dust ingestion. Moreover, the device of the present invention is not only inexpensive in construction and installation, but is also virtually fail-safe in operation.

BRIEF DESCRIPTION OF THE DRAWINGS

A better understanding of the present invention will be had upon reference to the following detailed description when read in conjunction with the accompanying drawing, wherein like reference characters refer to like parts throughout the several views, and in which.

DETAILED DESCRIPTION OF THE PRESENT INVENTION

Figure 1:
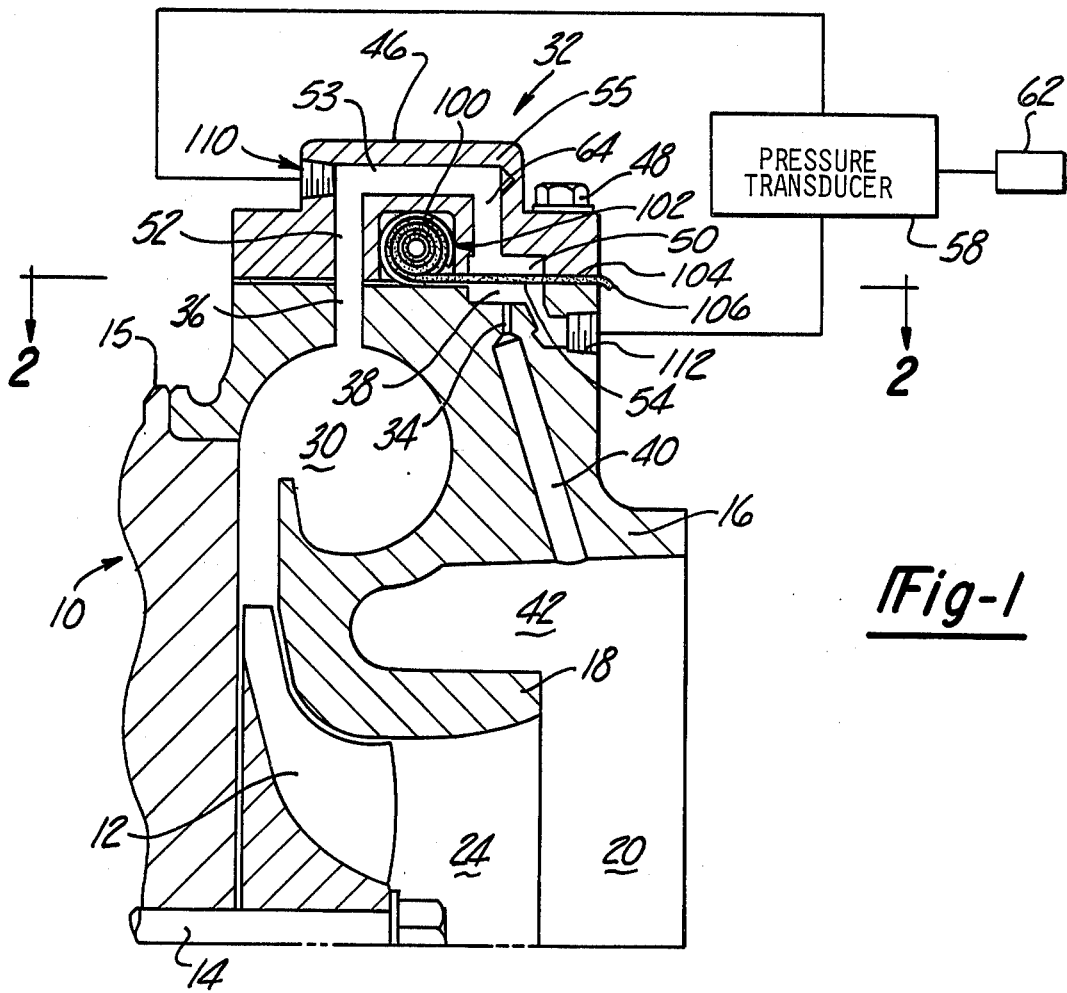
FIG. 1 is a fragmentary cross-sectional view illustrating the device of the present invention operatively installed in the air intake system of an internal combustion engine.
Figure 2:
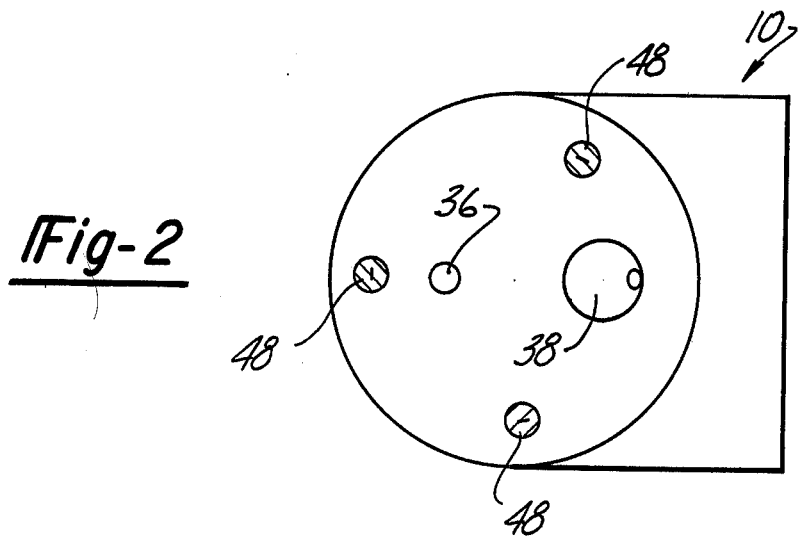
FIG. 2 is a partial sectional view taken substantially along line 2—2 in FIG. 1 and enlarged and with parts removed for clarity.

With reference first to FIG. 1, an engine turbocharger 10 is thereshown having a compressor rotor 12 rotatably mounted on an axle 14 within a turbocharger housing 16 of a main housing 15. The turbocharger housing 16 also includes an annular housing portion 18 which is concentric with and disposed around the compressor rotor 12.

An air inlet 20 supplies air from an air filtration means (not shown) and to the inlet 24 of the compressor rotor 12. Any conventional air filtration means can be used.

In the operation of the turbocharger 10, as the compressor rotor 12 rotates with the shaft 14, air is inducted through the air inlet 20, from the air filtration means and the fluid passageway 24 to the compressor rotor 12. The compressor rotor 12 compresses the air in an outlet chamber 30 and thereafter the compressed air is fed to an internal combustion engine (not shown) by appropriate passages (not shown).

The dust detector 32, according to the present invention, includes an outlet passage 36 formed through the turbocharger housing 16 which communicates at one end with the pressurized outlet chamber 30. The other end of the passage 36 communicates with a passage 52 of a housing cover 46.

A cylindrical lower filter chamber 38 is formed in the exterior of the turbocharger housing 16 at a position spaced opposite the passageway 50. The bottom of the lower filter chamber 38 communicates via a restricted port 34 and a fluid passageway 40 with an annular chamber 42 formed within the turbocharger housing 16 which in turn communicates with the inlet 20 of the compressor.

The housing 16 further includes a cover 46 detachably secured to the turbocharger housing 16 by means of bolts 48 so that the cover 46 covers and encloses the passageway 34 and lower filter chamber 38 on the turbocharger housing 16. An upper filter chamber 50 is formed within the cover 46 which registers with the lower filter chamber 38. In addition, a fluid passageway 52 is also provided within the cover 46 which is open at one end to the passageway 36 in the turbocharger housing 16 and connected by cross passages 53 and 64 to the upper filter chamber 50. With the cover 46 secured to the turbocharger housing 16 in the previously described fashion, a fluid passageway 55 comprising the passageways 36, 52, 53, and 64, the filter chambers 50 and 38, the restricted port 34 and the passageway 40 is formed between the compressor outlet chamber 30 and its inlet 24.

The cover 46 further includes a recess 100 formed between the passageway 52 and upper filter chamber 50. A filter strip dispenser or magazine 102 is positioned within the recess 100 and dispenses an elongated filter strip 104 between the cover 46 and housing 16, inbetween the filter chambers 50 and 38 and so that an end 106 of the filter strip 104 protrudes outwardly from between cover 46 and housing 16. The filter strip is coiled within the magazine 102. Alternatively, the filter strip can be simply coiled within the recess 100 and the magazine 102 can be eliminated.

An area portion of the filter strip 104 thus forms a filter element 54 which extends entirely across the filter chambers 50 and 38 so that the entire fluid flow through the filter chambers 50 and 38 passes through the filter element 54. Although the filter element 54 can be constrained between the filter chambers 50 and 38 in any desired fashion, preferably the filter strip 104 is sandwiched and compressed between the cover 46 and housing 16.

An inlet pressure tap 110 is open to the upper filter chamber 50 via the passageway 53 while, similarly, an outlet pressure tap 112 is open to the lower filter chamber 38. The pressure taps 110 and 112 are connected to a differential pressure transducer 58 which produces an output signal representative of the pressure drop across the filter element 54. Appropriate indicating and/or alarm means 62 are coupled to the transducer 58 to provide a signal representative of the transducer output.

The component parts of the dust detector 32 of the present invention having been described, the operation is as follows:

Assuming normal engine operation, air is inducted by the compressor rotor 12 through the inlet 20, from the air filtration means. The rotor 12 compresses this inlet air within the chamber 30 and the compressed air is then fed to the engine in the previously described fashion.

Due to the high pressure within the chamber 30, a portion of this air flows from the chamber 30 through the passageway 55 and thus through the filter element 54. The air pressure at the outlet 30 of the compressor rotor 12, of course, exceeds the air pressure at the rotor inlet 20 and the restricted port 34 minimizes the airflow through the passageway 55.

Further assuming that the engine air filtration means (not shown) is functioning in its proper and intended fashion, the air inlet provides only clean dust-free air at the compressor rotor inlet 24. Consequently, the air flow through the dust detector 32 is also dust free and the pressure drop across the filter element 54 sensed by the differential pressure transducer means 58 remains fairly small and within predetermined limits.

In the event of failure of the air filtration means (or equivalent failure), dust-laden air will be supplied to the compressor rotor inlet 24. The compressor rotor 12 compresses the dust-laden air within the outlet chamber 30 and a portion of this dust-laden air flows through the passageway 55 of the dust detector 32. The filament element 54 filters or removes the dust particles from the airflow in the conventional fashion.

As the filter element 54 becomes increasingly clogged with dust particles, the pressure drop across the filter element 54 likewise increases. This increased pressure drop is detected by the differential pressure transducer means 58 which generates appropriate signals to the indicating means 62. The indicating means 62 in turn signals the operator that the pressurized air in the outlet chamber 30, and consequently the air that is supplied to the engine, is dust-laden whereupon the operator can immediately shut down the engine and service the air filtration means.

Following the required maintenance on the air filtration system, the bolts 48 holding the cover 46 to the housing 16 are loosened and the filter strip 104 is grasped by its free end 106 and pulled outwardly away from the housing 16. In doing so, a clean portion of the filter strip 104 from the magazine 102 is positioned in between the fluid chambers 38 and 50. The cover 46 is then resecured to the housing 16 by tightening the bolts 48 and the dust detector 32 is again in a fully operational condition.

The dust detector 32 of the present invention, thus, provides a simple and economical means for detecting the presence of dust or other solid impurities in the pressurized air in the turbine compressor outlet 30. By early detection of dust in the passageway 30, prolonged dust ingestion by the engine can be avoided, thus, protecting the engine against damage caused by dust ingestion.

A still further advantage of the dust detector 32 of the present invention is that a clean portion of the filter strip 104 can be easily, rapidly and inexpensively positioned between the filter chambers 38 and 50 after clogging caused by dust ingestion.

While the dust detector 32 has been described for use with an engine turbocharger, it will be understood, of course, that the dust detector 32 can be used in conjunction with any pressurized fluid sufficient to cause a fluid flow through the passageway 55 of the dust detector 32.

Having described our invention, however, many modifications thereto will become apparent to those skilled in the art to which it pertains without deviation from the spirit of the invention as defined by the scope of the appended claims.

We claim:

1. A device for detecting solid or liquid impurities in a pressurized fluid comprising:
    a housing comprising a first part and a second part, said housing parts having mating surfaces and means for attaching said housing parts together so that said mating surfaces flatly abut against each other,
    said attaching means including means for variably compressing said housing parts together,
    a fluid pump contained in said first housing part, said pump having a high pressure outlet and a low pressure inlet,
    a first fluid passageway formed in said first housing part and extending from the fluid inlet and to the mating surface of the first housing part,
    a second fluid passageway formed in said first housing part and extending from the fluid outlet and to the mating surface of the first housing part,
    an interconnecting fluid passageway having a first and a second end and formed in said second housing part, each end of the interconnecting passageway being open to the mating surface on the second housing part, said first end being in registry with said first fluid passageway and said second end being in registry with the second fluid passageway when the mating surfaces abut against each other,
    means for dispensing an elongated filter strip, said dispensing means being positioned within a cavity formed in one of said mating surfaces, a portion of said filter strip extending from said dispensing means, between said mating surfaces and across one end of said interconnecting fluid passage, said filter strip having a free end accessible exteriorly of said housing, and
    pressure sensing means in communication with one of said fluid passageways.

2. The invention as defined in claim 1 wherein said fluid pump is a compressor rotor for a turbocharger of an internal combustion engine.

3. The invention as defined in claim 1 in which one of said fluid passageways includes a restricted port along its length.

4. The invention as defined in claim 3 wherein the restricted port is disposed in said first fluid and the passageway.

5. The invention as defined in claim 1 wherein the first fluid passageway is open to a chamber formed annularly around the pump inlet.

6. The invention as defined in claim 1 wherein said pressure sensing means further comprises means for sensing the differential pressure across the filter element.

7. The invention as defined in claim 1 wherein said dispensing means further comprises a coil of said filter strip.

8. The invention as defined in claim 1 wherein said attaching means comprises at least one bolt positioned through a hole in said second housing part and threadably engaging a threaded bore in the first housing part.

9. The invention as defined in claim 1 wherein said cavity is positioned in between the ends of the interconnecting fluid passageway.

* * * * *

UNITED STATES PATENT AND TRADEMARK OFFICE
CERTIFICATE OF CORRECTION

PATENT NO. : 4,263,805

DATED : April 28, 1981

INVENTOR(S) : Walter F. Isley and Joseph L. Dodd

It is certified that error appears in the above-identified patent and that said Letters Patent are hereby corrected as shown below:

Column 6, line 33, delete "and the".

Signed and Sealed this

Twenty-eighth Day of July 1981

[SEAL]

Attest:

Attesting Officer

GERALD J. MOSSINGHOFF

Commissioner of Patents and Trademarks